United States Patent
Leszko et al.

(10) Patent No.: US 10,039,645 B2
(45) Date of Patent: Aug. 7, 2018

(54) RELEASABLE THREADED CONNECTION FOR MODULAR IMPLANTS

(71) Applicant: DEPUY IRELAND UNLIMITED COMPANY, County Cork OT (IE)

(72) Inventors: Filip Leszko, West Chester, PA (US);
Aaron Matyas, Fort Wayne, IN (US);
Kyle Steffe, Warsaw, IN (US); David E. Rottger, Kendallville, IN (US);
Daniel M. Hippensteel, Fort Wayne, IN (US)

(73) Assignee: DePuy Ireland Unlimited Company, Cork (IE)

( * ) Notice: Subject to any disclaimer, the term of this patent is extended or adjusted under 35 U.S.C. 154(b) by 4 days.

(21) Appl. No.: 15/005,646

(22) Filed: Jan. 25, 2016

(65) Prior Publication Data

US 2017/0209279 A1    Jul. 27, 2017

(51) Int. Cl.
*A61F 2/38* (2006.01)
*A61F 2/46* (2006.01)
*A61F 2/30* (2006.01)

(52) U.S. Cl.
CPC .......... *A61F 2/3859* (2013.01); *A61F 2/389* (2013.01); *A61F 2/461* (2013.01); *A61F 2002/30329* (2013.01); *A61F 2002/30433* (2013.01); *A61F 2002/30434* (2013.01); *A61F 2002/30616* (2013.01); *A61F 2002/30772* (2013.01); *A61F 2002/30934* (2013.01); *A61F 2002/3863* (2013.01); *A61F 2002/4619* (2013.01); *A61F 2002/4638* (2013.01); *A61F 2220/0041* (2013.01)

(58) Field of Classification Search
USPC .......................................... 623/20.15, 20.35
See application file for complete search history.

(56) References Cited

U.S. PATENT DOCUMENTS

| 8,092,545 B2 | 1/2012 | Coon et al. |
| 8,092,546 B2 | 1/2012 | Coon et al. |
| 8,591,518 B2 | 11/2013 | Smith et al. |
| 9,168,156 B2 | 10/2015 | Crabtree et al. |

(Continued)

FOREIGN PATENT DOCUMENTS

| AU | 654364 B | 7/1992 |
| AU | 2005247033 A1 | 7/2006 |

(Continued)

*Primary Examiner* — David H Willse
*Assistant Examiner* — Javier Blanco
(74) *Attorney, Agent, or Firm* — Barnes & Thornburg LLP

(57) ABSTRACT

An orthopedic prosthesis assembly includes a first prosthetic component, a second prosthetic component, a retainer, and a fastener and allows the removal of the first prosthetic component without having to remove the second prosthetic component from an intramedullary canal of a patient's bone. The fastener is received in an aperture of the first prosthetic component and the retainer is configured to engage the aperture of the first prosthetic component such that a part of the fastener is secured within the aperture. A rod of the fastener is configured to advance along the longitudinal axis through the first prosthetic component into the second prosthetic component. The end of the rod of the fastener is threaded into a threaded bore defined in the second prosthetic component.

2 Claims, 7 Drawing Sheets

(56) References Cited

U.S. PATENT DOCUMENTS

| | | | |
|---|---|---|---|
| 9,615,930 B2 | 4/2017 | Katrana | |
| 9,629,724 B2 | 4/2017 | Lappin | |
| 2009/0306787 A1* | 12/2009 | Crabtree | A61F 2/4684 |
| | | | 623/20.34 |
| 2014/0276883 A1* | 9/2014 | Matyas | A61B 17/921 |
| | | | 606/99 |
| 2017/0100176 A1 | 4/2017 | Kumar | |

FOREIGN PATENT DOCUMENTS

| | | |
|---|---|---|
| AU | 2014201451 A1 | 10/2014 |
| CN | 103070738 A | 5/2013 |

\* cited by examiner

RELEASABLE THREADED CONNECTION FOR MODULAR IMPLANTS

TECHNICAL FIELD

The present disclosure relates generally to an implantable orthopaedic prosthesis, and more particularly to an implantable knee prosthesis.

BACKGROUND

During the lifetime of a patient, it may be necessary to perform a joint replacement procedure on the patient as a result of, for example, disease or trauma. The joint replacement procedure may involve the use of a primary prosthesis which is implanted into one or more of the patient's bones. In the case of a knee replacement procedure, a tibial tray is implanted into the patient's tibia. A bearing is secured to the tibial tray. The condyle surfaces of a replacement femoral component bear against the tibial bearing.

Such a primary knee prosthesis may also include a number of elongated intramedullary stem components and optional prosthetic components (e.g., sleeves and/or adaptors) which are implanted in the patient's tibia and/or femur. To secure a stem component and/or other components to the patient's tibia and/or femur, the intramedullary canal of the patient's tibia and/or femur is first surgically prepared (e.g., reamed) such that the stem component and/or other components may be subsequently implanted therein. In some designs, the stem component is implanted in the patient's bone by use of cementless fixation. One type of such a design is known as a 'press fit' stem component.

On occasion, the primary knee prostheses fails. Failure can result from many causes, including wear, aseptic loosening, osteolysis, ligamentous instability, arthrofibrosis and patellofemoral complications. When the failure is debilitating, revision knee surgery may be necessary. In a revision, the primary knee prosthesis is removed and replaced with components of a revision prosthetic knee system.

Various orthopaedic surgical instruments are used throughout such an orthopaedic procedure. For example, bone saws and/or reamers may be use to surgically prepare a bone surface to accept an orthopaedic implant. Additionally, depending on the particularly implant, a variety of orthopaedic surgical instruments may be used to assembly, disassembly, and/or install the orthopaedic implant into the prepared bone.

SUMMARY

According to one aspect of the disclosure, an orthopaedic surgical instrument is disclosed. The orthopaedic surgical instrument includes a first prosthetic component, a second prosthetic component, a retainer, and a fastener. The first prosthetic component includes an outer surface, an inner surface, and a post. The inner surface is positioned opposite the outer surface that is configured to face a bone of a patient. The post extends from the inner surface along a longitudinal axis. The post includes an opening defined in a free end and an inner wall that extends inwardly from the opening to define an aperture in the post. The second prosthetic component including a first end, a second end opposite the first end, and a threaded bore defined in the first end. The retainer is secured within the aperture of the post adjacent to the free end and includes a central bore that extends along the longitudinal axis of the post. The fastener includes a head and a threaded rod. The head is configured to be positioned in the aperture of the first prosthetic component. The head has a dimension greater than the central bore such that the head is retained in the aperture. The threaded rod extends away from the head through the central bore of the retainer to an end positioned beyond the free end of the post. The threaded rod of the fastener is configured to be engaged with the threaded bore of the second prosthetic component to secure the first prosthetic component to the second prosthetic component.

In some embodiments, the inner wall of the post of the first prosthetic component may include a threaded surface adjacent to the free end of the post. The retainer may further include a threaded outer surface that is engaged with the threaded surface of the inner wall to secure the retainer within the aperture of the post.

In some embodiments, the outer surface of the first prosthetic component may include an opening defined therein, and a passageway extends inwardly from the opening to the aperture.

In some embodiments, the orthopaedic surgical instrument further includes a tool having an end. The end is sized to be received in the passageway and configured to engage the head of the fastener and selectively rotate the fastener to secure the first prosthetic component to the second prosthetic component.

In some embodiments, when the tool is rotated in a first direction, the threaded rod is advanced into the threaded bore of the second prosthetic component. When the tool is rotated in a second direction opposite the first direction, the threaded rod is moved out of engagement with the threaded bore.

In some embodiments, the first prosthetic component may be a femoral component having a pair of condyle surfaces.

In some embodiments, the second prosthetic component may be a stem component having an elongated body extending from the first end.

In some embodiments, the second prosthetic component may include a sleeve component.

In some embodiments, the first prosthetic component may be a tibial component comprising a tibial tray having a platform and the post extends from the platform.

In some embodiments, the second prosthetic component may be a stem component having an elongated body extending from the first end.

According to another aspect, an orthopaedic prosthesis system includes a tibial tray component, a stem component, a retainer, and a fastener. The tibial component further includes a platform and a post. The platform includes a proximal surface configured to receive a tibial insert component and a distal surface opposite the proximal surface. The post extends from the distal surface along a longitudinal axis. The post includes an opening defined in a free end and an inner wall that extends inwardly from the opening to define an aperture in the post. The stem component includes a first end, an elongated body extending from the first end, and a threaded bore defined in the first end. The retainer is secured within the aperture of the post adjacent to the free end. The retainer includes a central bore that extends along the longitudinal axis of the post. The fastener further includes a head and a threaded rod. The head is positioned in the aperture of the tibial tray component. The head has a dimension greater than the central bore such that the head is retained in the aperture. The threaded rod extending away from the head through the central bore of the retainer to an end positioned beyond the free end of the post. The threaded rod of the fastener is configured to be engaged with the threaded bore of the stem component to secure the tibial tray component to the stem component.

In some embodiments, the inner wall may include a threaded surface adjacent to the free end of the post. The retainer may include a threaded outer surface that is engaged with the threaded surface of the inner wall to secure the retainer within the aperture of the post.

In some embodiments, the proximal surface of the tibial tray component may have an opening defined therein, and a passageway extends inwardly from the opening to the aperture.

In some embodiments, the orthopaedic prosthesis system further includes a tool having an end sized to be received in the passageway and is configured to engage the head of the fastener and selectively rotate the fastener to secure the tibial tray component to the stem component.

In some embodiments, when the tool is rotated in a first direction, the threaded rod is advanced into the threaded bore of the stem component. When the tool is rotated in a second direction opposite the first direction, the threaded rod is moved out of engagement with the threaded bore.

According to another aspect, an orthopaedic prosthesis system includes a femoral component, a stem component, a retainer, and a fastener. The femoral component further includes a pair of condyle surfaces, a fixation surface positioned opposite the pair of condyle surfaces, and a post extending from the fixation surface along a longitudinal axis. The post includes an opening defined in a free end and an inner wall that extends inwardly from the opening to define an aperture in the post. The stem component further includes a first end, an elongated body extending from the first end, and a threaded bore defined in the first end. The fastener includes a head and a threaded rod. The head is positioned in the aperture of the femoral component and has a dimension greater than the central bore such that the head is retained in the aperture. The threaded rod extends away from the head through the central bore of the retainer to an end positioned beyond the free end of the post. The threaded rod of the fastener is configured to be engaged with the threaded bore of the stem component to secure the femoral component to the stem component.

In some embodiments, the inner wall may include a threaded surface adjacent to the free end of the post. The retainer may include a threaded outer surface that is engaged with the threaded surface of the inner wall to secure the retainer within the aperture of the post.

In some embodiments, the fixation surface of the femoral component may have an opening defined therein, and a passageway extends inwardly from the opening to the aperture.

In some embodiments, the orthopaedic prosthesis system may further include a tool having an end. The end is sized to be received in the passageway and is configured to engage the head of the fastener and selectively rotate the fastener to secure the femoral component to the stem component.

In some embodiments, when the tool is rotated in a first direction, the threaded rod is advanced into the threaded bore of the stem component. When the tool is rotated in a second direction opposite the first direction, the threaded rod is moved out of engagement with the threaded bore.

BRIEF DESCRIPTION OF THE DRAWINGS

The detailed description particularly refers to the following figures, in which.

DETAILED DESCRIPTION OF THE DRAWINGS

Figure 1:
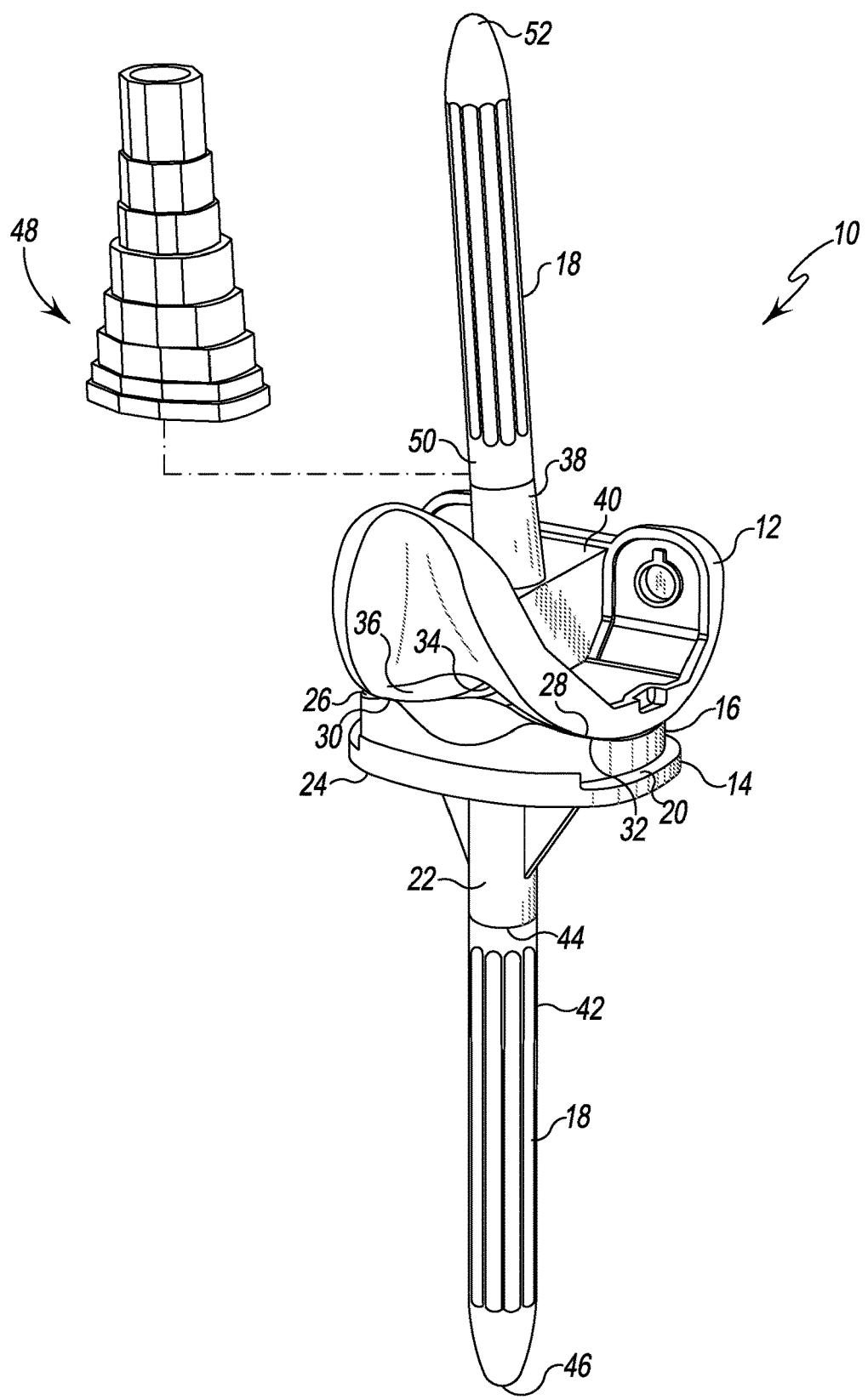
FIG. 1 is a perspective view of an implantable orthopaedic knee prosthesis assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring to FIG. 1, an implantable orthopaedic knee prosthesis assembly 10 for use in the performance of an orthopaedic knee replacement procedure is shown. The knee prosthesis assembly 10 includes a femoral component 12, a tibial tray component 14, and a bearing 16. The knee prosthesis assembly 10 also includes a stem component 18 secured to the femoral component 12 and a stem component 18 secured to the tibial tray component 14. As will be described in detail below, each of the components 12, 14 is secured to the stem component 18 via a retained fastener such that each component 12, 14 can be disassembled from the stem component 18 and separately removed from the patient's bone during the revision process. The fastener is retained in the component 12, 14 by a retainer such that the fastener does not detach from the tibial tray component 14 during the revision process.

Figure 3:
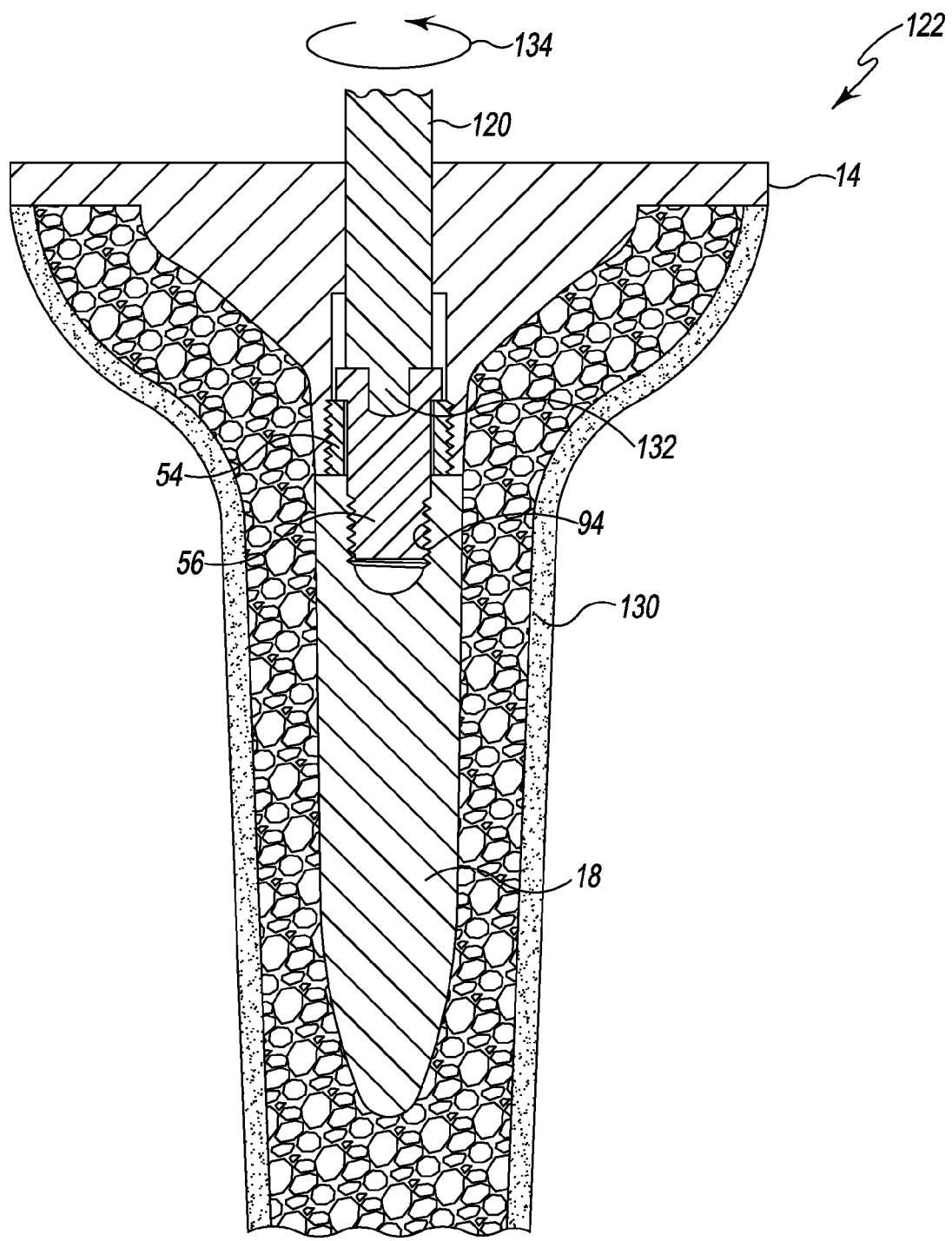
FIG. 3 is a cross sectional elevation view illustrating the tibial tray component secured to a stem component in a patient's tibia.

The tibial tray component 14 is configured to be implanted into a surgically-prepared proximal end of a patient's tibia 130 (see FIG. 3). The tibial tray component 14 includes a platform 20 and an elongated tibial stem post 22 extending inferiorly away from the inferior surface 24 of the platform 20. The tibial stem post 22 is configured to engage the stem component 18, as will be described in more detail below.

The bearing 16 is securable to the tibial tray component 14. In particular, the bearing 16 may be snap-fitted into the tibial tray component 14 such that the bearing 16 is fixed relative to the tibial tray component 14 (i.e., it is not rotatable or moveable in the anterior/posterior or medial/lateral directions). In other embodiments, the bearing 16 may be secured in a manner that allows it to rotate relative to the tibial tray component 14. The bearing 16 includes a lateral bearing surface 26 and a medial bearing surface 28. The bearing surfaces 26, 28 are configured to articulate with a lateral condyle surface 30 and a medial condyle surface 32, respectively, of the femoral component 12. Specifically, the femoral component 12 is configured to be implanted into a surgically-prepared distal end of a patient's femur 140, and is configured to emulate the configuration of the patient's natural femoral condyles. As such, the lateral condyle surface 30 and the medial condyle surface 32 are configured (e.g., curved) in a manner which mimics the condyles of the natural femur. The lateral condyle surface 30 and the medial condyle surface 32 are spaced apart from one another thereby defining an intercondylar notch 34 therebetween.

The condyle surfaces 30, 32 are formed in a bearing surface 36 of the femoral component 12. The femoral component 12 also includes an elongated stem post 38, extending superiorly away from its opposite backside surface 40. The elongated femoral stem post 38 is configured to engage the stem component 18, as will be discussed in more detail below. The stem component 18 and the femoral component 12 may be implanted into a surgically-prepared (e.g., reamed or broached) patient's femur 140 (see FIG. 6).

As shown in FIG. 1, each of the stem components 18 includes an elongated, generally cylindrical stem body 42. The elongated stem body 42 further includes a threaded bore 124 at a proximal end 44 thereof (see FIGS. 4 and 6-7). When the stem component 18 is secured to the tibial tray component 14, the elongated stem body 42 of the stem component 18 extends distally away from the distal end of the post 22 of the tray 14 and terminates at rounded distal end 46 that defines the inferior-most surface of the stem component 18. When the stem component 18 is secured to the femoral component 12, the elongated stem body 42 of the stem component 18 extends proximally away from the distal end 50 of the femoral component 12 and terminates at rounded proximal end 52 that defines the superior-most surface of the stem component 18.

The stem component 18 may be provided in a number of different configurations in order to fit the needs of a given patient's anatomy. In particular, the stem component 18 may be configured in various different lengths to conform to the patient's anatomy (e.g., a relatively long stem component 18 for use with a long femur or tibia, a relatively short stem component 18 for use with a short femur or tibia, etcetera). The stem component 18 may also be provided in varying body diameters to fit the needs of a given patient's anatomy. The body diameter of a given stem component 18 is the stem component's medial/lateral cross sectional width in the cylindrical midsection of the stem component's body (i.e., not at its tapered post or its distal tip). In other embodiments, the stem component 18 may have some other shape (e.g., non-cylindrical) and size. Likewise, the femoral component 12 and the tibial tray component 14 may be provided in various different sizes to fit the needs of a given patient's anatomy.

The knee prosthesis assembly 10 may also include a number of optional components in various embodiments. For example, the knee prosthesis assembly 10 may include a femoral sleeve component 48. The femoral sleeve component 48 may be used to facilitate implantation of the femoral component 12 in the presence of reduced bone quality in the patient's femur 140. The femoral sleeve component 48 is configured to be secured to the femoral component 12 so as to be positioned between the femoral component 12 and the stem component 18.

Figure 2:
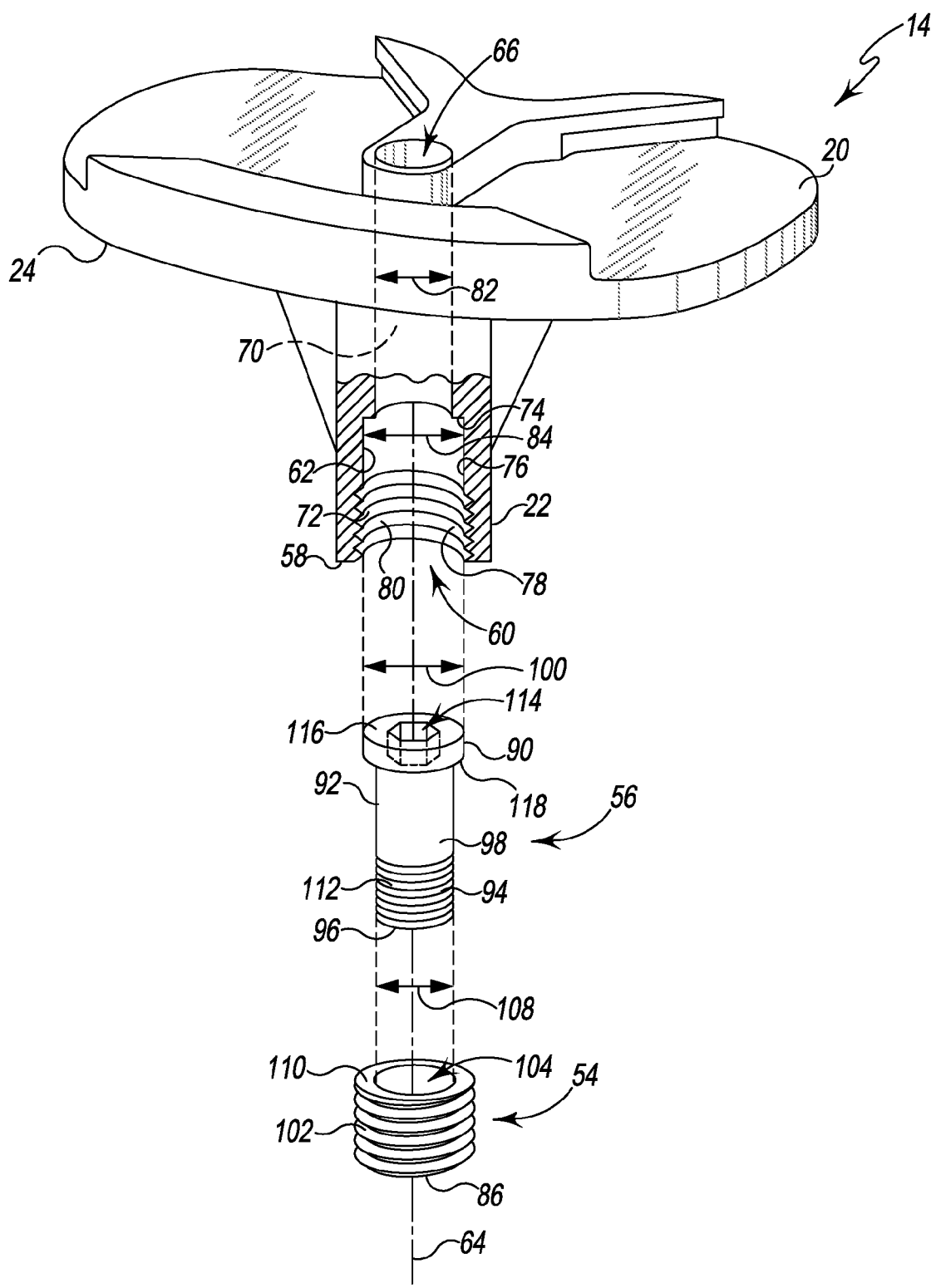
FIG. 2 is an exploded, partial cross-section perspective view of a tibial tray component, a fastener, and a retainer of the implantable orthopaedic knee prosthesis assembly of FIG. 1.

Referring now to FIG. 2, the tibial tray component 14 is shown with a retainer 54 that is configured to be secured to the post. As described in greater detail below, the retainer 54 is configured to capture the fastener 56 to prevent the fastener 56 from becoming detached from the tibial tray component 14. In the illustrative embodiment, the elongated tibial stem post 22 extends inferiorly away from the inferior surface 24 to a distal end 58. The tibial stem post 22 further includes an opening 60 defined in the distal end 58 and an inner wall 62 that extends inwardly from the distal opening 60 along the longitudinal axis 64 to a proximal opening 66 defined in the platform 20 of the tibial tray component 14. The inner wall 62 of the tibial tray component 14 defines an upper passageway 70 and a lower passageway 72. A rim surface 74 of the inner wall 62 is defined at the intersection of the upper passageway 70 and the lower passageway 72.

The upper passageway 70 extends inferiorly away from the proximal opening 66 of the platform 20 to the rim surface 74 of the tibial stem post 22. The lower passageway 72 extends inferiorly from the rim surface 74 to the distal opening 60 and includes a superior section 76 and an inferior section 78. The inferior section 78 is defined by a plurality of internal threads 80 configured to receive corresponding threads of the retainer 54. In some embodiments, the entire inner wall 62 in the lower passageway 72 of the tibial tray component 14 may be threaded. In the illustrative embodiment, the superior section 76 includes a substantially smooth cylindrical surface Further, the upper passageway 70 has a diameter 82 smaller than a diameter 84 of the lower passageway 72 such that the rim surface 74 is defined between a distal end of the upper passageway 70 and a proximal end of the lower passageway 72 as shown in FIG. 2. The larger lower passageway 72 is configured to receive the head of the fastener 56 and the smaller upper passageway 70 is configured to receive a surgical instrument tool 120, as will be described in more detail below.

Figure 4:
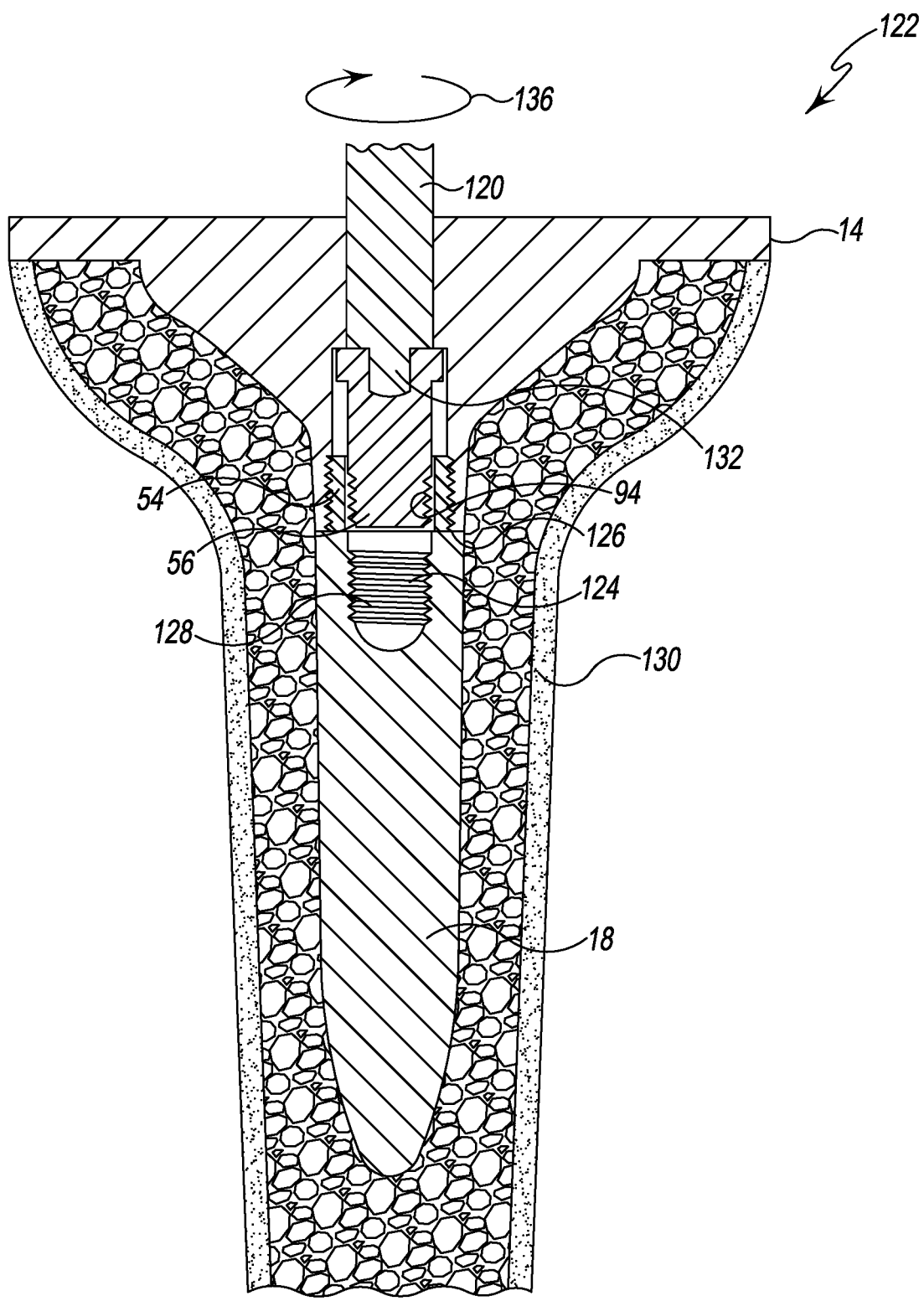
FIG. 4 is a view similar to FIG. 3 illustrating the tibial tray component decoupled from the stem component in the patient's tibia.

In the illustrative embodiment of FIGS. 2-4, the fastener 56 is a screw. It should be appreciated, however, that the fastener 56 may be any fastening device or component configured to extend through the tibial tray component 14 to the stem component 18 to secure the tibial tray component 14 to the stem component 18. As shown in FIG. 2, the fastener 56 includes a head 90 and an elongated shaft 92 extending away from the head 90. The elongated shaft 92 has a threaded section 94 at a base 96 of the fastener 56 opposite the head 90 and a substantially smooth unthreaded section 98 between the threaded section 94 and the head 90. In some embodiments, the entire elongated shaft 92 of the fastener 56 may be threaded.

The head 90 of the fastener 56 is configured to be received in the lower passageway 72 of the tibial tray component 14 and has a diameter 100 greater than a diameter 82 of the upper passageway 70 of the tibial tray component 14. Accordingly, when the fastener 56 is positioned within the lower passageway 72 of the tibial tray component 14, the head 90 may advance through the tibial stem post 22 of the tibial tray component 14 along the longitudinal axis 64 but does not pass beyond the rim surface 74 into the upper passageway 70. After the fastener 56 is positioned in the lower passageway 72 of the tibial tray component 14, the lower passageway 72 may receive the retainer 54 to secure the fastener 56 in the tibial tray component 14.

The retainer 54 includes a plurality of external threads 102 and a central bore 104 extending longitudinally thereof. The central bore 104 of the retainer 54 is configured to receive the elongated shaft 92 of the fastener 56 to secure the tibial stem post 22 and the stem component 18. The external threads 102 of the retainer 54 are configured to be threaded into the internal threads 80 of the lower passageway 72 of the tibial tray component 14 to position the retainer 54 in the tibial tray component 14. In some embodiments, the retainer 54 may be snap-fitted into the lower passageway 72 of the tibial tray component 14, thereby fixing the retainer 54 into the tibial stem post 22 of the tibial component 14.

As shown in FIG. 2, the retainer 54 has a length shorter than a length of the elongated shaft 92 of the fastener 56 and the central bore 104 of the retainer 54 has an inner diameter 106 larger than the outer diameter 108 of the elongated shaft 92 of the fastener 56. Further, the head 90 of the fastener 56 has the diameter 100 greater than the diameters 106, 108 of the central bore 104 of the retainer 54 and the elongated shaft 92 of the fastener 56. Accordingly, as the elongated shaft 92 of the fastener 56 passes through the central bore 104 of the retainer 54, a lower surface 118 of the head 90 of the fastener 56 is configured to rest on the proximal end 110 of the retainer 54 but not pass through the central bore 104 of the retainer 54. When the head 90 rests atop the retainer 54, the elongated shaft 92 is positioned within the central bore 104 of the retainer 54 such that the threaded section 94 of the elongated shaft 92 extends beyond the distal end 86 of the retainer 54. The threaded section 94 of the elongated shaft 92 includes a plurality of threads 112 configured to engage the stem component 18, as will be discussed in more detail below.

The head 90 of the fastener 56 further includes a tool socket 114 in an upper surface 116 of the head 90. The tool socket 114 is shaped to accept a surgical instrument tool 120. For example, the tool socket 114 may be hex-shaped to accept a hex driver. The tool socket 114 may be otherwise shaped to accept a surgical instrument tool head 132 of a different shape.

Referring now to FIGS. 3-4, an orthopaedic surgical procedure using a tibial component assembly 122 including the tibial tray component 14, the retainer 54, the fastener 56, and the stem component 18 is shown. As described above, the stem component 18 includes a threaded bore 124 defined in a proximal end 126 of the stem component 18. The threaded bore 124 is defined by a plurality of threads 128 configured to receive the threaded section 94 of the fastener 56 to secure the stem component 18 to the tibial tray component 14.

As shown in FIG. 3, the tibial component assembly 122 is positioned in the intramedullary canal of the patient's surgically prepared tibia 130. During a primary implantation procedure, the patient's tibia 130 may be surgically prepared (e.g., reamed) to remove patient's damaged bone. Subsequently, the primary tibial component assembly 122 may be impacted into the intramedullary canal of the patient's surgically prepared tibia 130.

The primary tibial component assembly 122 may be assembled before implantation by inserting the head 90 of the fastener 56 through the distal opening 60 of the tibial tray component 14. As described above, the head 90 may advance through the lower passageway 72 of the tibial tray component 14 along the longitudinal axis 64 but may not pass the rim surface 156 into the upper passageway 70. The elongated shaft 92 of the fastener 56 may then be inserted through the central bore 104 of the retainer 54. The external threads 102 of the retainer 54 may be threaded into the internal threads 80 of the lower passageway 72 of the tibial tray component 14. This configuration allows the head 90 of the fastener 56 to be securely coupled to the tibial tray component 14. Specifically, the head 90 of the fastener 56 is secured within the superior section 76 of the lower passageway 72 of the tibial tray component 14 between the rim surface 74 and the proximal end 110 of the retainer 54. After the fastener 56 and the retainer 54 are inserted into the tibial tray component 14, the surgeon may use the tool 120 to engage the tibial tray component 14 and the stem component 18. The surgeon may advance the tool head 132 of the tool 120 through the proximal opening 66 along the upper passageway 70 into the tool socket 114 of the fastener 56. The surgeon may then rotate the tool 120 to thread the threaded section 94 of the fastener 56 into the threaded bore 124 of the stem component 18, thereby securing the tibial tray component 14 and the stem component 18.

If a surgical revision of the prosthesis may become necessary, the surgeon may disassemble the tibial component assembly 122 to replace some components. During the orthopaedic knee revision procedure, the surgeon may disassemble the tibial component assembly 122 by removing the tibial tray component 14 while the stem component 18 positioned the intramedullary canal of a patient's tibia 130. In the illustrative embodiment, removing the tibial tray component 14 from the stem component 18 may involve unscrewing the fastener 56 from the stem component 18 until the threaded section 94 of the fastener 56 is completely detached from the threaded bore 124 of the stem component 18. To do so, the surgeon may advance the tool head 132 of the tool 120 through the proximal opening 66 along the upper passageway 70 into the tool socket 114 of the fastener 56 as shown in FIG. 4.

As described above, the tool 120 includes a tool head 132 having a shape matching that of the tool socket 114 of the fastener 56. For example, if the fastener 56 is a hex screw, a hex driver may be used to remove the fastener 56 from the stem component 18. As shown in FIG. 3, when the tool head 132 is properly inserted into the tool socket 114, the surgeon may rotate the surgical instrument tool 120 in a first direction 134, causing the threaded section 94 of the fastener 56 to disengage from the threaded bore 124 of the stem component 18. The surgeon may continue to rotate the fastener 56 to extract the fastener 56 from the stem component 18, as shown in FIG. 3. The surgeon may then pull the tool 120 upwardly through the upper passageway 70 away from the stem component 18. As described previously, when the tibial tray component 14 is completely detached from the stem component 18, the fastener 56 remains coupled to the tibial tray component 14 via the retainer 54. The surgeon may remove the tibial tray component 14 from the patient's bone using another tool before removing the stem component 18 from the intramedullary canal of the patient's tibia 130. Subsequently, the surgeon may assemble a revision tibial component assembly 122 and may implant the revision tibial component assembly 122 back into the intramedullary canal of the patient's tibia 130.

In some embodiments, the stem component 18 may remain in the intramedullary canal of the patient's tibia 130. Subsequently, the surgeon may assemble the tibial component assembly 122 by attaching a revision tibial tray component 14 to the stem component 18 positioned in the patient's tibia 130. To do so, the surgeon may align the threaded section 94 of the fastener 56 with the threaded bore 124 of the stem component 18. The tool 120 is then used to screw the fastener 56 into the stem component 18 by rotating the threaded section 94 of the fastener 56 into the threaded bore 124 of the stem component 18 toward a second direction 136 opposite the first direction 134 as shown in FIG. 4. As the tool 120 rotates, the threaded section 94 of the fastener 56 is threaded into the threaded bore 124 of the stem component 18, thereby securing the tibial tray component 14 to the stem component 18.

Figure 5:
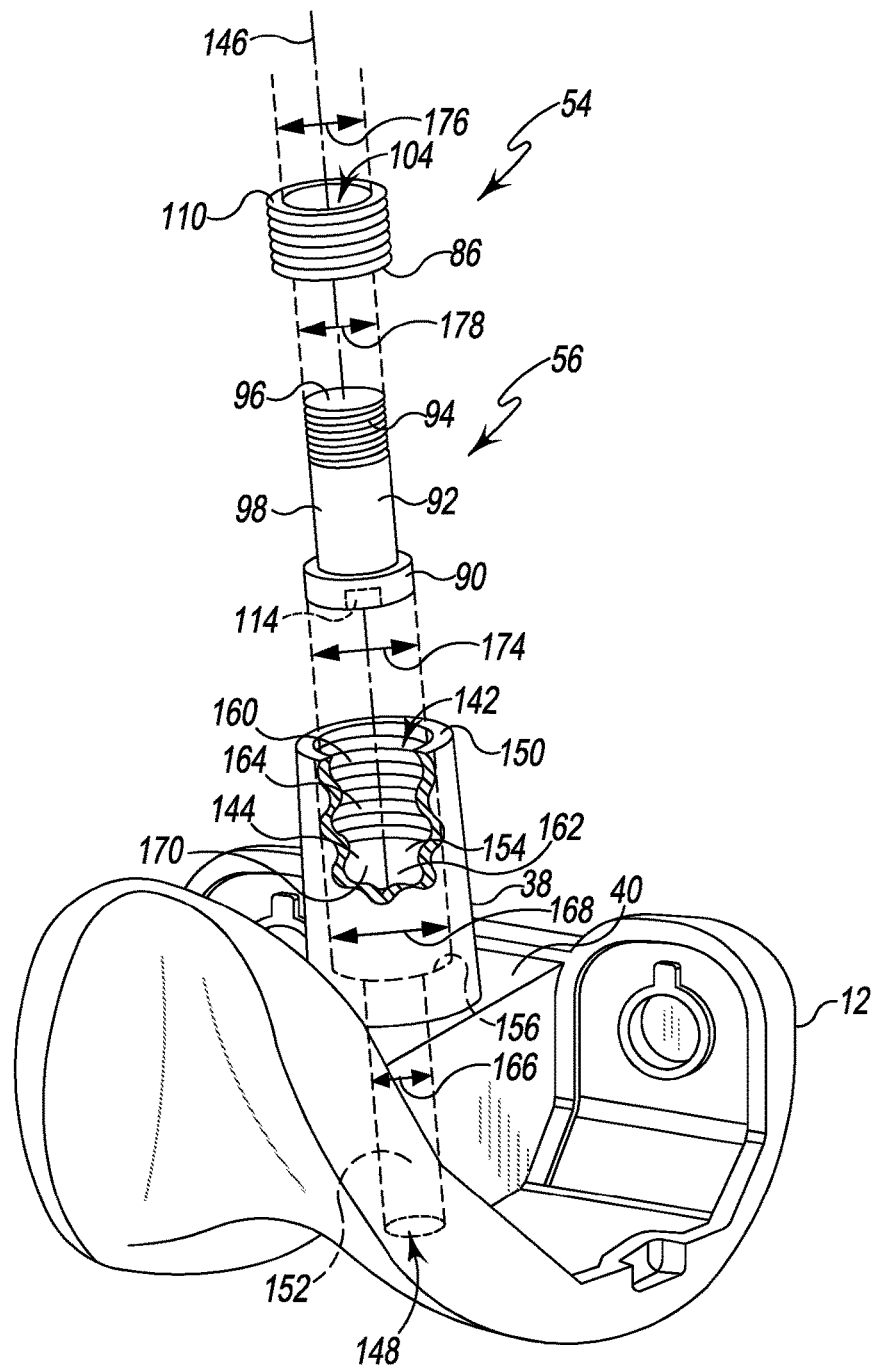
FIG. 5 is an exploded, partial cross-section perspective view of a femoral component, a fastener, and a retainer of the implantable orthopaedic knee prosthesis assembly of FIG. 1.

Referring now to FIG. 5, an exploded view of the femoral component 12 with a retainer 54 and a fastener 56 is shown. As described above, the femoral component 12 includes the elongated stem post 38 extending superiorly away from its opposite backside surface 40. The elongated femoral stem post 38 is configured to engage a stem component 18. The assembly may then be implanted into a surgically-prepared (e.g., reamed or broached) intramedullary canal of the patient's femur 140.

Similar to the tibial stem post 22 of the tibial tray component 14, the elongated femoral stem post 38 further includes a proximal opening 142 and an inner wall 144 that extends inwardly from the proximal opening 142 along the longitudinal axis 146 to a distal opening 148 defined in an intercondylar notch 34 of the femoral component 12. The proximal opening 142 is defined in the proximal end 150 of the femoral stem post 38 and the inner wall 144 extends inwardly from the proximal opening 142 along the longitudinal axis 146. The inner wall 144 of the femoral component 12 defines a lower passageway 152 and an upper passageway 154. A rim surface 156 of the inner wall 144 is defined at the intersection of the lower passageway 152 and the upper passageway 154.

The lower passageway 152 extends superiorly away from the distal opening 148 of the femoral component 12 to the rim surface 156 of the femoral stem post 38. The upper passageway 154 extends superiorly from the rim surface 156 to the proximal opening 142 at the proximal end 150 of the femoral stem post 38. Similar to the lower passageway 72 of the tibial tray component 14, the upper passageway 154 of the femoral component 122 includes a superior section 160 and an inferior section 162. The superior section 160 is defined at the proximal end 150 of the upper passageway 154 by a plurality of inner threads 164 that are configured to receive corresponding threads of the retainer 54. In some embodiments, the entire inner wall 144 in the upper passageway 154 of the femoral component 12 may be threaded.

Further, the lower passageway 152 has a diameter 166 smaller than a diameter 168 of the upper passageway 154 such that the rim surface 156 is defined between a distal end of the upper passageway 154 and a proximal end of the lower passageway 152 as shown in FIG. 5. The larger upper passageway 154 is configured to receive the head of the fastener 56 and the smaller lower passageway 152 is configured to receive a surgical instrument tool 120, as will be described in more detail below.

As described above, the retainer 54 has a length shorter than a length of the elongated shaft 92 of the fastener 56 and the central bore 104 of the retainer 54 has an inner diameter 106 larger than an outer diameter 108 of the elongated shaft 92 of the fastener 56. Further, the head 90 of the fastener 56 has an outer diameter 174 greater than the diameters 176, 178 of the central bore 104 of the retainer 54 and the elongated shaft 92 of the fastener 56. Accordingly, as the elongated shaft 92 of the fastener 56 passes through the central bore 104 of the retainer 54, the head 90 of the fastener 56 is configured to contact the distal end 86 of the retainer 54 but not pass through the central bore 104 of the retainer 54. When the head 90 is in contact with the retainer 54, the elongated shaft 92 is positioned within the central bore 104 of the retainer 54 such that the threaded section 94 of the elongated shaft 92 extends beyond the proximal end 110 of the retainer 54. The threaded section 94 of the elongated shaft 92 includes a plurality of threads 112 configured to engage the stem component 18, as will be discussed in more detail below.

The head 90 of the fastener 56 further includes a tool socket 114 in an upper surface 116 of the head 90. The tool socket 114 is shaped to accept a surgical instrument tool 120. For example, the tool socket 114 may be hex-shaped to accept a hex driver. The tool socket 114 may be otherwise shaped to accept a surgical instrument tool head 132 of a different shape.

Figure 6:
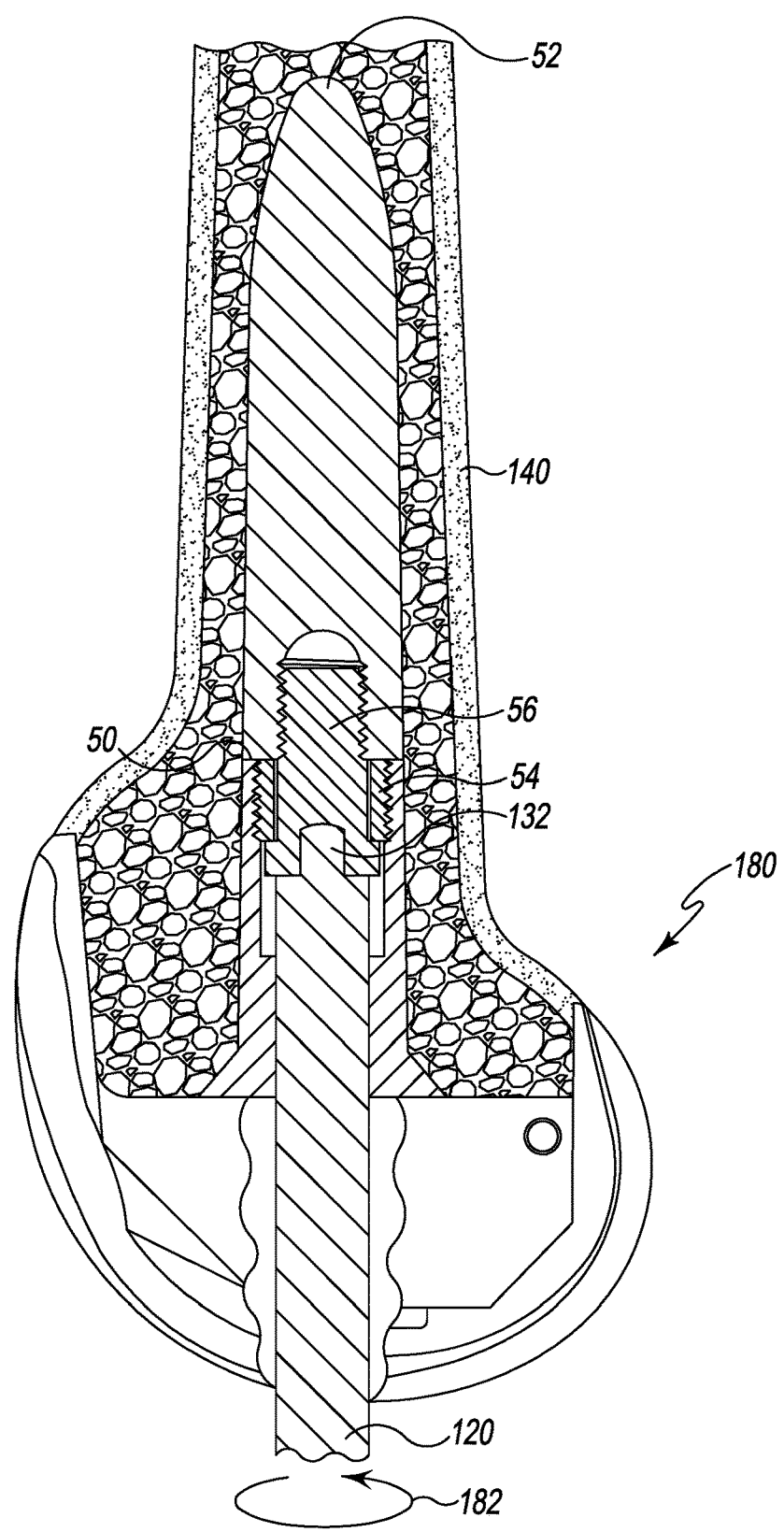
FIG. 6 is a cross sectional elevation view illustrating the femoral component secured to a stem component in the patient's femur.
Figure 7:
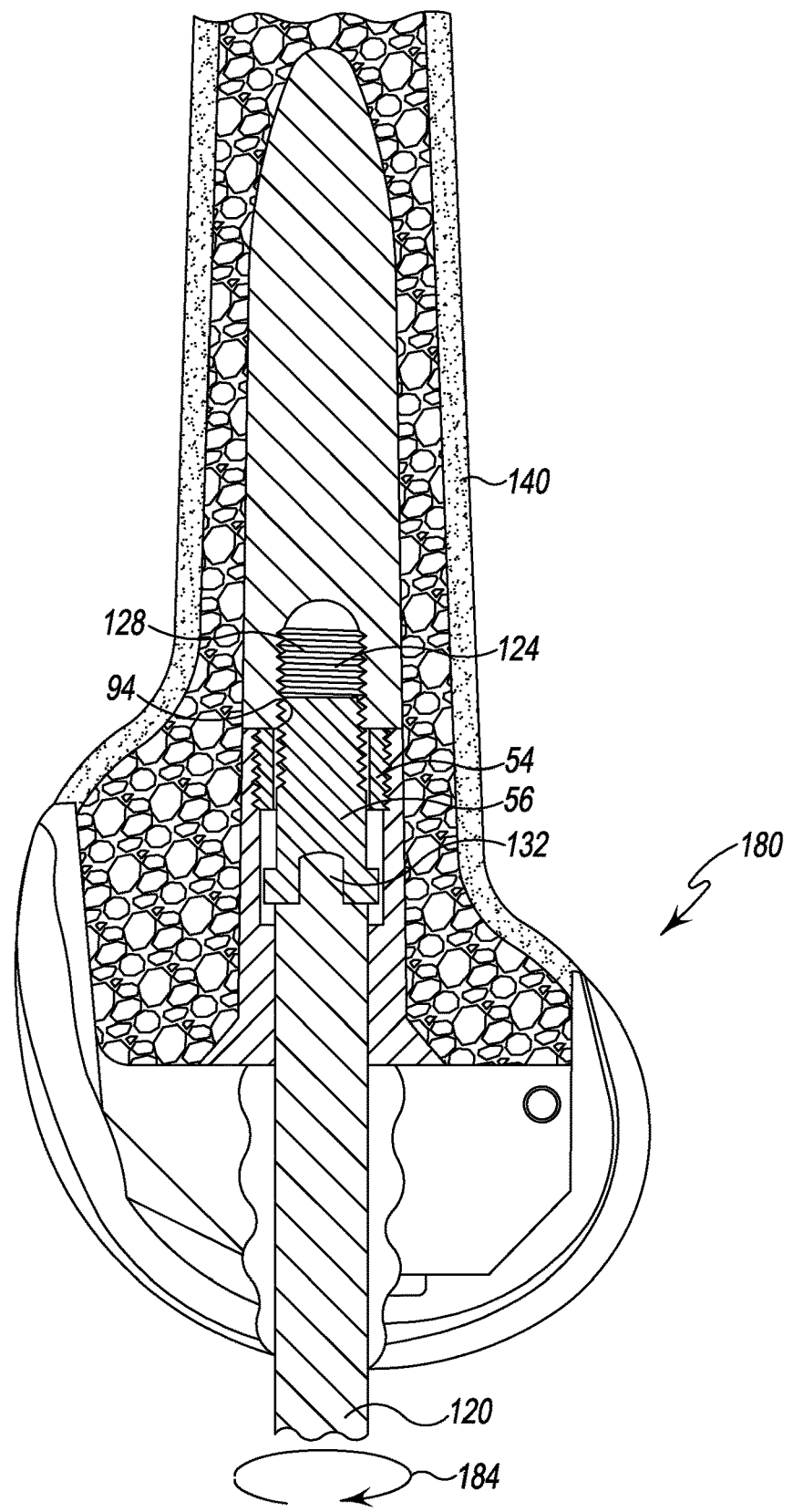
FIG. 7 is a view similar to FIG. 6 illustrating the femoral component decoupled from the stem component in the patient's femur.

Referring now to FIGS. 6-7, an orthopaedic surgical procedure using a femoral component assembly 180 including the femoral component 12, the retainer 54, the fastener 56, and the stem component 18 is shown. The stem component 18 includes a threaded bore 124 defined in a distal end 50 of the stem component 18. The threaded bore 124 is defined by a plurality of threads 128 configured to receive the threaded section 94 of the fastener 56 to secure the stem component 18 to the femoral component 12.

As shown in FIG. 6, the femoral component assembly 180 is positioned in the intramedullary canal of the patient's surgically prepared femur 140. During a primary orthopaedic knee replacement procedure, the patient's femur 140 may be surgically prepared (e.g., reamed) to remove patient's damaged bone. Subsequently, the primary femoral component assembly 180 may be impacted into the intramedullary canal of the patient's surgically prepared femur 140, as shown in FIG. 6

The femoral component assembly 180 may be assembled before implantation by inserting the head 90 of the fastener 56 through the proximal opening 142 of the femoral component 12. As described above, the head 90 of the fastener 56 may advance through the upper passageway 154 of the femoral component 12 along the longitudinal axis 146 but may not pass the rim surface 156 into the lower passageway 152. The elongated shaft 92 of the fastener 56 may then be inserted through the central bore 104 of the retainer 54. The external threads 102 of the retainer 54 may be threaded into the inner threads 164 of the upper passageway 154 of the femoral component 12. This configuration allows the head 90 of the fastener 56 to be securely coupled to the femoral component 12. Specifically, the head 90 of the fastener 56 is secure within the inferior section 170 of the upper passageway 154 of the femoral component 12 between the rim surface 156 of the femoral component 12 and the distal end 86 of the retainer 54. After the fastener 56 and the retainer 54 are attached to the femoral component 12, the surgeon may use the tool 120 to engage the femoral component 12 and the stem component 18. The surgeon may advance the tool head 132 of the tool 120 through the distal opening 148 along the lower passageway 152 into the tool socket 114 of the fastener 56. The surgeon may then rotate the tool 120 to thread the threaded section 94 of the fastener 56 into the threaded bore 124 of the stem component 18, thereby securing the femoral component 12 to the stem component 18.

If a surgical revision of the prosthesis may become necessary, the surgeon may disassemble the femoral component assembly 180 to replace some components. Specifically, the surgeon may remove the femoral component 12 separately from the stem component 18 positioned in the patient's femur 140. In the illustrative embodiment, removing the femoral component 12 from the stem component 18 may involve unscrewing the fastener 56 from the stem component 18 until the threaded section 94 of the fastener 56 is completely detached from the threaded bore 124 of the stem component 18. To do so, the surgeon may advance the tool head 132 of the tool 120 through the distal opening 148 along the lower passageway 152 into the tool socket 114 of the fastener 56, as shown in FIG. 6.

The surgical instrument tool 120 may be used to unthread the threaded section 94 of the fastener 56 from the threaded bore 124 of the stem component 18 to disassemble the femoral stem post 38 of the femoral component 12 from the stem component 18. As described above, the tool 120 includes the tool head 132 having a shape matching that of the tool socket 114 of the fastener 56. When the tool head 132 is properly inserted into the tool socket 114, the surgeon may rotate the surgical instrument tool 120 in a first direction 182 until the fastener 56 is completely extracted from the stem component 18. The surgeon may then pull the tool 120 through the lower passageway 152 away from the stem component 18. When the femoral component 12 is completely detached from the stem component 18, the fastener 56 remains coupled to the femoral component 12 via the retainer 54. The surgeon may then remove the femoral component 12 from the patient's femur before removing the stem component 18 from the intramedullary canal. Subsequently, the surgeon may assemble a revision femoral component assembly 180 and may implant the revision femoral component assembly 180 back into the intramedullary canal of the patient's femur 140.

In some embodiments, the stem component 18 may remain in the intramedullary canal of the patient's femur 140. Subsequently, the surgeon may assemble the femoral component assembly 180 by attaching a revision femoral component 12 to the stem component 18 positioned in the patient's femur 140. To do so, the surgeon may align the threaded section 94 of the fastener 56 with the threaded bore 124 of the stem component 18 as shown in FIG. 7. The tool 120 is then used to screw the fastener 56 into the stem component 18 by rotating the threaded section 94 of the fastener 56 into the threaded bore 124 of the stem component 18 toward a second direction 184 opposite the first direction 182. As the tool 120 rotates, the threaded section 94 of the fastener 56 is threaded into the threaded bore 124 of the stem component 18, thereby securing the tibial tray component 14 to the stem component 18.

The femoral component assembly 180 may further include the femoral sleeve component 48 as described above. The femoral sleeve component 48 is configured to be secured to the femoral component 12 so as to be positioned between the femoral component 12 and the stem component 18. In particular, the inferior end of the femoral sleeve component 48 has an opening (not shown) formed therein that may be taper-fitted to the outer surface of the stem post 38 of the femoral component 12 to secure the femoral sleeve component 48 to the femoral component 12. The opposite, superior end of the femoral sleeve component 48 is configured to be attached to the stem components 18 via a fastener 56. The femoral sleeve component 48 further includes a passageway (not shown) extending inwardly from the opening of the inferior end of the femoral sleeve component 48 to the superior end of the femoral sleeve component 48.

In such embodiment, the fastener 56 has the head 90 and the elongated shaft 92 having a length longer than a length of the femoral sleeve component 48. Accordingly, the elongated shaft 92 of the fastener 56 extends through the passageway of the femoral sleeve component 48 such that the threaded section 94 of the fastener 56 extends beyond the femoral sleeve component 48. The threaded section 94 of the fastener 56 may then engage the threaded bore 124 of the stem component 18 to secure the femoral stem post 38 to the stem component 18.

During an orthopaedic knee revision procedure, the femoral component 12, the fastener 56, and the retainer 54 may be accessed from the distal end of the patient's femur. The surgeon may disassemble the femoral component assembly 180 with the femoral sleeve component 48 while the stem component 18 is positioned in the intramedullary canal of patient's bone. The disassembly process may be similar to that described above in FIGS. 6-7 using the surgical tool 120.

It should be appreciated that the methods described herein permit a surgeon to assemble or disassemble orthopaedic prosthetic component assemblies from the joint line within the patient's bone. While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There is a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An orthopaedic modular knee prosthesis system, comprising:
    a femoral component including (i) a pair of condyle surfaces sized to articulate with a tibial bearing, wherein the pair of condyle surfaces are spaced apart from one another thereby defining an intercondylar notch therebetween, (ii) a distal opening defined in the intercondylar notch, (iii) a fixation bone-contacting surface positioned opposite the pair of condyle surfaces and configured to engage a femur of a patient, and (iv) an elongated stem-mounting post extending from the fixation bone-contacting surface along a longitudinal axis, the post including a proximal opening defined in a free end and an inner wall that extends inwardly from the proximal opening along the longitudinal axis to the distal opening, wherein (a) the inner wall of the post defines a first cylindrical passageway extending from the distal opening, a second cylindrical passageway in the post, and an inner rim surface at an intersection of the first cylindrical passageway and the second cylindrical passageway, (b) the first cylindrical passageway extends from the distal opening to the inner rim surface, and the second cylindrical passageway extends from the inner rim surface to the proximal opening, (c) the second cylindrical passageway includes a plurality of internal threads, and (d) the second cylindrical passageway has a diameter larger than a diameter of the first passageway,
    a femoral stem component adapted to be implanted into a surgically-prepared patient's femur, the femoral stem component including (i) a first end, (ii) an elongated body extending from the first end, and (iii) a threaded bore defined in the first end, a cylindrical retainer secured within the second cylindrical passageway of the post adjacent to the free end, the retainer including (i) a central bore that extends along the longitudinal axis of the post, and (ii) a threaded outer surface that is engaged with the internal threads of the second cylindrical passageway to secure the retainer within the second cylindrical passageway of the post, a fastener having (i) a head positioned in the second cylindrical passageway, the head having a diameter greater than a diameter of the central bore of the retainer and greater than the diameter of the first cylindrical passageway such that the head is retained in the second cylindrical passageway between the retainer and the inner rim surface and does not pass beyond the inner rim surface and into the first cylindrical passageway when the fastener is positioned in the second cylindrical passageway, and (ii) a threaded rod extending away from the head through the central bore of the retainer to an end positioned beyond the free end of the post, and a surgical instrument tool having an end sized to be received in the first cylindrical passageway, wherein the threaded rod of the fastener is configured to be engaged with the threaded bore of the stem component to secure the femoral component to the stem component, wherein, when the end of the surgical instrument tool is received in the first cylindrical passageway, said end is configured to engage the head of the fastener and selectively rotate the fastener to secure the femoral component to the stem component.

2. The orthopaedic modular knee prosthesis system of claim 1, wherein when the tool is rotated in a first direction, the threaded rod of the fastener is advanced into the threaded bore of the stem component, and when the tool is rotated in a second direction opposite the first direction, the threaded rod is moved out of engagement with the threaded bore.

* * * * *